(12) United States Patent
Elliott

(10) Patent No.: US 6,900,361 B2
(45) Date of Patent: May 31, 2005

(54) PROCESS FOR LACTOSE CONVERSION TO POLYOLS

(75) Inventor: Douglas Charles Elliott, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 107 days.

(21) Appl. No.: 09/851,678

(22) Filed: May 8, 2001

(65) Prior Publication Data

US 2002/0169344 A1 Nov. 14, 2002

(51) Int. Cl.⁷ .......................... C07C 31/18; C07C 31/20; C07C 31/22; C07C 31/24; C07C 29/14
(52) U.S. Cl. ...................... 568/863; 435/105; 435/158; 435/159
(58) Field of Search .................. 568/863; 435/105, 435/158, 159

(56) References Cited

U.S. PATENT DOCUMENTS

| | | | |
|---|---|---|---|
| 2,004,135 A | 6/1935 | Rothrock | |
| 2,518,235 A | 8/1950 | Hartstra et al. | |
| 2,868,847 A | 1/1959 | Boyers | |
| 3,471,580 A | 10/1969 | Hellwig et al. | |
| 3,538,019 A | 11/1970 | Capik et al. | |
| 4,067,748 A | * 1/1978 | Rowe | ........................... 127/36 |
| 4,380,678 A | 4/1983 | Sirkar | |
| 4,409,247 A | * 10/1983 | Baret et al. | .................... 426/41 |
| 4,430,253 A | 2/1984 | Dubeck et al. | |
| 5,354,914 A | 10/1994 | Gubitosa et al. | |
| 5,814,112 A | 9/1998 | Elliott et al. | |
| 6,152,975 A | 11/2000 | Elliott et al. | |

FOREIGN PATENT DOCUMENTS

| | | |
|---|---|---|
| WO | WO 98/37204 | 8/1998 |
| WO | WO 01/17677 | 3/2001 |

OTHER PUBLICATIONS

Yamaguchi et al., *J. Biochem.* 82(6):1673–1680, 1977.
Hu et al., *J. Agric. Food Chem.*, 44:3757–3762, 1996.

* cited by examiner

*Primary Examiner*—Elvis O. Price
(74) *Attorney, Agent, or Firm*—Klarquist Sparkman, LLP

(57) ABSTRACT

A process for converting lactose into polyols that includes (a) hydrolyzing lactose to produce a hydrolyzate that includes at least one monosaccharide, (b) subsequently hydrogenating the hydrolyzate to produce an alditol-containing intermediate composition, and (c) hydrogenolyzing the alditol-containing intermediate composition to produce at least one polyol.

35 Claims, No Drawings

PROCESS FOR LACTOSE CONVERSION TO POLYOLS

FIELD OF THE DISCLOSURE

The present disclosure relates to a process for converting lactose into polyols, particularly lower carbon polyols.

BACKGROUND

Cheese whey is a byproduct of cheese production. Lactose and protein are the two major components of whey. Lactose recovery from whey has increased steadily over the past years, but lactose remains an underutilized commodity. The value of lactose could be increased if efficient, inexpensive methods existed for converting lactose to higher value chemicals.

Various techniques for converting lactose into other compounds or materials are known. One approach has been to directly hydrogenate lactose to obtain its sugar alcohols, lactitol and lactulitol (see Hu et al., "HPLC and NMR Study of the Reduction of Sweet Whey Permeate", J. Agric. Food Chem. 44, 3757–3762 (1996)). However, further processing of the sugar alcohol product stream from such a direct hydrogenation produces a wide variety of components ranging from high molecular weight $C_{12}$ products to lower carbon polyhydric alcohols such as ethylene glycol, propylene glycol and glycerol. Thus, the yield of the lower carbon polyols is less than desirable and significant multiple steps are required for separating the various product components.

A further carbohydrate hydrogenation example is mentioned in U.S. Pat. No. 4,430,253 ("Dubeck"). Dubeck describes a two-stage process for converting carbohydrates to lower carbon polyhydric alcohols. The first stage is a hydrogenation of the carbohydrate to obtain a higher carbon polyhydric alcohol and the second stage is a hydrogenolysis of the higher carbon polyhydric alcohol to obtain the lower carbon polyhydric alcohol. Lactose is included in a list of possible carbohydrates that could undergo conversion according to the process described in Dubeck, but there are no working examples describing conversion of any di- or polysaccharide. Preferred di- or polysaccharide starting materials "are those which are readily hydrolyzable to monosaccharides under dilute acid conditions" (column 3, lines 61–63). Dubeck does not appear to contemplate a continuous process that includes a separate hydrolysis step prior to the hydrogenation. It is stated that "polysaccharides are hydrolyzed to their basic monosaccharide (or monosaccharides) whose aldehyde or ketone groups are then hydrogenated to hydroxyl groups to produce the desired polyhydric alcohol (or alcohols) of the monosaccharide" (column 4, lines 53–57). However, Dubeck teaches that "those polysaccharides having free aldehyde or ketone groups in their molecular structure may have these groups hydrogenated at the same time the molecule is hydrolyzed" (column 4, lines 57–60). The Dubeck disclosure goes on to indicate that a mineral acid "can be added to the first stage reaction medium, either at the outset or during the reaction, e.g., between the first and second stages (the latter is ordinarily preferred), for pH control" (column 6, lines 21–25). Unfortunately, simultaneous hydrogenation and hydrolysis of a disaccharide as suggested by Dubeck tends to reduce product selectivity due to hydrogenation of the disaccharide directly to a $C_{12}$ alditol and over-reaction via the hydrolysis mechanism to undesired hydrolyzate products, such as hydroxymethylfurfurals. Moreover, the addition of a mineral acid such as sulfuric acid or phosphoric acid can cause contamination of the downstream products and poison the hydrogenation catalyst.

Another example of a lactose manipulation is acid hydrolysis of a partial amount of lactose in a sugar composition in order to sweeten the taste of the composition. However, the currently commercialized processes are terminated prior to achieving hydrolysis of substantially all of the lactose since their objective is not complete conversion of the lactose-containing mixture.

Various techniques for converting glucose to lower carbon polyols are known. For example, U.S. Pat. No. 4,380,678 ("Sirkar") describes a multi-stage method for converting aldoses to glycerol and other polyols. The Sirkar process involves a first step of catalytically hydrogenating the aldoses to obtain their respective alditols and then subjecting the alditols to catalytic hydrogenolysis to obtain glycerol and other polyols.

In summary, the existing processes for lactose conversion all suffer from significant drawbacks. Thus, a continuing need exists for an efficient, inexpensive method for converting lactose to higher value chemicals.

SUMMARY OF THE DISCLOSURE

Disclosed are various processes for converting lactose into easily recoverable, higher value-added polyols. According to one embodiment the lactose conversion method includes (a) hydrolyzing lactose to produce a hydrolyzate that includes at least one monosaccharide, (b) subsequently hydrogenating the hydrolyzate to produce an alditol-containing intermediate composition, and (c) hydrogenolyzing the alditol-containing intermediate composition to produce at least one polyol. According to a second embodiment the lactose conversion method includes (a) heating lactose in the presence of water and a solid acid catalyst or enzyme to produce a first intermediate, (b) subsequently heating the first intermediate in the presence of hydrogen and a catalyst to produce a second intermediate, and (c) heating the second intermediate in the presence of hydrogen, a catalyst, and a base to produce at least one polyol. A feature of these processes is that the lactose is hydrolyzed prior to hydrogenation. Such hydrolysis prior to hydrogenation can lead to advantageous yields of valuable lower carbon polyols such as ethylene glycol, propylene glycol and glycerol.

One variant of the lactose conversion method involves employing a hydrogenation catalyst that includes ruthenium disposed on a titania support. Such a ruthenium catalyst is very selective towards producing desired alditols such as sorbitol and dulcitol and is exceptionally stable in aqueous medium reaction environments. A further variant involves catalytically hydrolyzing the lactose wherein the hydrolysis catalyst may be a solid acid or an immobolized enzyme. Utilization of a solid acid or an immobolized enzyme avoids the downstream contamination and catalyst poisoning problems associated with a liquid acid or free enzyme catalyst.

The foregoing features and advantages will become more apparent from the following detailed description of several embodiments.

DETAILED DESCRIPTION OF SEVERAL EMBODIMENTS

The following definitions are provided for ease of understanding and to guide those of ordinary skill in the art in the practice of the embodiments.

A "continuous method" contemplates a multi-step process wherein the steps are performed in a manner such that a reactant stream flows continuously through the stages (e.g., reactors) defined by the steps. Of course, the continuous flow does not have to be on a constant 24/7 hours/days basis (i.e., there can be down times for maintenance, process adjustment or simple lack of demand).

"Higher carbon polyhydric alcohol" denotes a polyhydric alcohol that includes more than five carbon atoms.

"Lactose" includes both lactose and isomers thereof having a $C_{12}H_{22}O_{11}$ formula such as, for example, lactulose.

"Lower carbon polyhydric alcohol or polyol" denotes a polyhydric alcohol or polyol, respectively, that includes less than six carbon atoms.

"Polyhydric alcohol" denotes an alcohol that includes at least two hydroxy groups.

"Polyol" includes both polyhydric alcohols and polyhydric phenols.

As described above, the disclosed methods include at least three steps. According to certain embodiments, the first step converts the lactose (a disaccharide) to monosaccharides (typically the $C_6$ aldose constituents of lactose, glucose and galactose). The monosaccharides then are converted in the second step to their respective higher carbon polyhydric alcohols. For example, glucose and galactose are converted to their respective alditols, sorbitol and dulcitol. The third step involves "hydrocracking" the higher carbon polyhydric alcohols by breaking the carbon-carbon bonds to produce lower carbon polyhydric alcohols. For example, sorbitol and dulcitol are hydrocracked to lower carbon polyhydric alcohols. The conversion end products may especially include dihydric alcohols such as ethylene glycol or propylene glycol and trihydric alcohols such as glycerol. This three-step conversion scheme may have a yield of at least about 50, more particularly about 70, weight percent lower carbon polyhydric alcohols based on the total amount theoretically available in the lactose feed stock.

The lactose used as the starting material or feedstock for the disclosed processes may be dissolved in an aqueous medium or phase. For example, the lactose may be mixed with water in an amount of at least about 5 weight %, more particularly at least about 15 weight %, most particularly about 5 to about 20 weight %, dry solids lactose based on the total weight of aqueous lactose composition. A primary source for an aqueous lactose-containing composition is whey. In particular, an aqueous lactose product may be refined from whey permeate via known techniques. Alternatively, unrefined lactose-containing whey permeate may be used directly as the feedstock.

The hydrolysis of the lactose may be a catalytic hydrolysis such as an enzymatic hydrolysis, an acid hydrolysis or a combination thereof. The hydrolysis is carried out in the presence of water, typically the water that is included in an aqueous lactose feedstock. The hydrolysis may be continued until substantially all of the lactose available for conversion has been hydrolyzed. In particular, the hydrolysis reaction conditions can be selected to maximize the conversion of the lactose to the monosaccharides. For example, about 90 to about 100 weight %, more particularly about 99 to about 100 weight %, of the lactose may be hydrolyzed during the first step into monosaccharides.

In accordance with the enzymatic hydrolysis embodiment, a single enzyme or mixture of enzyme(s) may be added to the lactose feedstock. Suitable enzyme(s) are those that have hydrolytic reactivity for lactose. Illustrative enzymes include β-galactosidase as produced by *aspergillus oryzae* fungi or *Kluyveromyces lactis* yeast. The enzyme(s) may be used in its immobilized form. Immobilized enzyme(s) can be more stable in a processing environment and their movement is limited (i.e., they remain in the hydrolysis reactor and do not contaminate the downstream process). Immobolized β-galactosidase is commercially available, for example, from Valio Engineering, Ltd. of Helsinki, Finland under the trade designation "IML". The amount of enzyme added may vary and typically is dependent upon the reaction temperature and pH.

The enzyme(s) is added to the lactose feedstock and the resulting mixture typically is subjected to a temperature of about 5 to about 50° C., more particularly about 5 to about 20° C., during the hydrolysis. The pH of the hydrolysis reaction mixture may be maintained at a pH ranging from about 3 to about 7, more particularly about 3.5 to about 4.5 for fungal enzymes and about 7 for yeast-derived enzymes. The pH of the lactose feedstock is typically in the range of about 3 to about 7, but a small amount of acid may be added if pH adjustment is required. The operating pressure during the enzymatic hydrolysis reaction is not critical and may be maintained, for example, at about 1 atmosphere.

The acid hydrolysis step may be effected by heating the lactose feedstock in the presence of an acid catalyst. In particular, the aqueous lactose feedstock may be heated at a temperature of about 50 to about 100° C., more particularly about 80 to about 100° C.

The acid hydrolysis catalyst may be any type of catalyst capable of initiating and sustaining hydrolysis of a di- or polysaccharide. Illustrative classes of such catalysts include liquid (i.e., free) acids or solid acids. Possible liquid or free acids include sulfuric acid or hydrochloric acid. Examples of possible solid acid catalysts include acidic ion exchange resins such as a cation resin like sulphonated polystyrene (commercially available from Applexion, Inc. of Des Plaines, Ill.), or a perfluorinated polymeric resin (commercially available from DuPont Co. under the trade designation NAFION). Although liquid or free acids may be used in certain embodiments, utilization of a solid acid catalyst avoids contamination and catalyst poisoning problems associated with liquid or free acids.

If a solid acid catalyst is employed, the acid hydrolysis reaction may be carried out under basic, neutral or acidic conditions. If base is present, its reaction with the solid acid will tend to degrade the solid acid while exchanging protons into solution, causing neutralization of the solution and adsorption of the basic cations onto the solid acid resin. The two-fold effect will be to de-mineralize the hydrolyzed lactose stream and cause a need for regeneration of the sold acid catalyst. According to particular embodiments, for example, the reaction medium may be maintained at a pH of about 2 to about 10, more particularly about 4 to about 7.

The hydrolysis step can be performed as a batch operation or as a continuous flow operation. In the case of a batch operation, the particular time required to achieve the desired substantially complete conversion varies depending upon the other reaction conditions but, for example, may range from about 10 to about 100 minutes. In the case of continuous flow operation with a catalyst bed reactor, the space velocity through the reactor varies depending upon the other reaction conditions but, for example, may range from about 0.1 to about 2 volumes of solution per volume of solid catalyst bed per hour (i.e., liquid hourly space velocity—"LHSV").

The hydrolyzate resulting from the hydrolysis step includes at least one monosaccharide, and is typically an aqueous mixture of monosaccharides. In the case of lactose itself in the initial feedstock the resulting monosaccharides are primarily glucose and galactose. If lactulose is also included in the initial feedstock, then fructose will be an additional resulting monosaccharide.

The hydrolysis in the first step may be substantially completed prior to beginning the following hydrogenation step. In other words, the hydrolysis and the hydrogenation preferably do not occur simultaneously.

The hydrogenation step involves heating the hydrolyzate in the presence of hydrogen and a catalyst. An advantage of the disclosed process is that the hydrogenation may be performed directly on the hydrolyzate mixture without the need for any prior separation or purification of the hydrolyzate. The hydrogenation is continued until a desired amount of the monosaccharide(s) are converted to their corresponding alditol(s). For example, at least about 90 to about 100, more particularly at least about 99 to about 100, weight percent of the monosaccharide(s) may be converted to alditol(s). The product resulting from the hydrogenation may be an aqueous mixture of alditols, primarily sorbitol and dulcitol (and mannitol if lactulose is included in the initial feedstock).

According to specific embodiments of the hydrogenation, the aqueous hydrolyzate is heated at a temperature of about 80 to about 180° C., more particularly about 100 to about 120° C. The pH of the hydrogenation reaction medium is not critical and may be acidic, neutral or basic. The system pressure during the hydrogenation step also may vary and could range, for example, between about 200 to about 3000, more particularly about 1000 to about 1500, psig. The hydrogen reactant typically may be contacted with the hydrolyzate by flowing hydrogen gas into the reaction system via known means. The hydrogen may be fed into the reaction system with an overpressure in order to maintain the desired reaction system pressure.

The hydrogenation catalyst may be any type of catalyst capable of initiating and sustaining hydrogenation of a monosaccharide. Such catalysts are well known and typically are metal catalysts such as ruthenium, nickel (e.g., Raney nickel), cobalt, copper and alloys thereof. The metal catalysts may be provided on various support substrates such as titania, zirconia, alumina, silica, alumina/silica and carbon. According to certain embodiments, the catalyst support is especially stable in aqueous medium or phase chemical reaction conditions. "Stable" means that the support remains physically intact and chemically inert. Exemplary stable supports include titania in the rutile form, zirconia in the monoclinic form, high-surface area granulated carbons, or boehmite.

A particular example of an especially useful hydrogenation catalyst is a ruthenium disposed on a titania support. Illustrative ruthenium/titania support catalysts are described in PCT Publication WO 01/17677, published Mar. 15, 2001. For example, the ruthenium may constitute about 0.1 to about 10, particularly about 1 to about 5, and more particularly about 2 to about 3, weight percent of the catalyst. The ruthenium is disposed on a titania support. According to certain embodiments, the ruthenium may exist as small particles on the surface of the support. The surface of the support typically includes not only the exterior surfaces but also interior surfaces of a porous support. The support may be in a variety of forms such as powder, pellets, honeycomb, etc. The titania may be composed of at least about 75 weight percent, particularly about 90 weight percent, or more particularly about 95 weight percent, rutile. The weight percent rutile is measured as follows. A powdered sample of the support (or catalyst) is analyzed by x-ray diffraction using a copper x-ray source operating at 45 kV and 40 mA scanning over the range of 5 to 75 degrees across 2-theta. The rutile and anatase phases can be identified by comparison with database reference patterns. The peak height of the largest rutile peak and largest anatase peak are used for quantitation. The % rutile is determined as a percentage of its peak height divided by the sum of the heights of the largest rutile and largest anatase peaks. The support may be at least about 90 weight percent titania, more particularly at least about 99.5 weight percent titania.

Although it is possible to generate a rutile support in situ by selection of processing conditions that favor the formation of rutile, better and more consistent activity and stability can be achieved by using a support with a high level of rutile (at least about 75 weight percent, more preferably about 90 weight percent, and still more preferably about 95 weight percent) prior to depositing ruthenium on the support's surface. Titania supports having a high level of rutile phase can be purchased or prepared. A suitable support is P25 code 7709 titania, available from Degussa Corporation, Parsippany, N.J., USA. This support can be used without additional calcination or thermal processing. Alternatively, titania can be prepared by known methods such as oxidation of titanium chloride and hydrolysis of titanium alkoxides. The support can be titania powder, or in the form of tablets, pellets, extrudates or other forms for use in a fixed bed catalyst system.

Ruthenium can be co-precipitated with titania, but for greater activity and economy it can be deposited onto the titania support. The ruthenium can be deposited onto a titania support by impregnating with aqueous ruthenium compositions such as aqueous ruthenium chloride. Other methods such as vapor deposition are also possible. After impregnation, water is removed by heating and the precipitated ruthenium compound is reduced to the metal by reduction with hydrogen at elevated temperature.

This ruthenium catalyst may be provided essentially without nickel, that is, nickel does not make a significant contribution to the catalytic activity of the catalyst. For example, the catalyst may contain less than about 0.1 weight percent nickel, more particularly, less than about 0.01 weight percent. The catalyst may also be provided essentially without rhenium. This means that the rhenium to ruthenium ratio in the catalyst can be less than about 1:20 by weight. Rhenium, if present at all, may be present in less than about 0.005 weight percent of the catalyst. Similarly, the catalyst may be provided essentially without cobalt.

It has been found that when glucose is the feedstock for hydrogenation with such a ruthenium catalyst, the hydrogenation has a high selectivity for sorbitol (as opposed to mannitol or other alditols). For example, hydrogenation of a glucose feedstock (concentration of 40 weight % glucose in water, 1900 psig $H_2$, at a temperature of 100° C., and a liquid hourly space velocity of about 4) in the presence of a ruthenium on rutile catalyst results in at least about 98% conversion of the glucose and at least about 95% selectivity for sorbitol. The ruthenium catalyst allows for lower operating temperatures and higher processing rates compared to other hydrogenation catalysts.

Another example of a particularly useful hydrogenation catalyst is a catalyst in the form of a plurality of porous particles wherein each particle is a support having nickel metal catalytic phase or reduced nickel deposited thereon as a dispersed phase and an additional metal deposited onto the support as an additional dispersed phase as described, for example, in U.S. Pat. Nos. 5,814,112 and 6,152,975, both incorporated herein by reference. The additional metal is effective in stabilizing (i.e., retarding or reducing agglomeration or sintering) the nickel metal catalytic phase thereby increasing the effective lifetime of the catalyst.

For example, the dispersed reduced nickel phase may be a reduced nickel/copper catalytic alloy having substantially more reduced nickel than copper and the additional metal dispersed phase for agglomeration resistance may be a second alloy of nickel or reduced nickel and copper having substantially more copper than nickel. Alternatively, the added metal may simply be a non-alloyed copper. According to other embodiments the additional metal is a separate and distinct phase from the dispersed nickel phase and prevents or retards agglomeration of the nickel phase between catalyst particles. The amount of added metal may be less than or equal to about 5 weight percent, more particularly less than about 2 weight percent, and most particularly from about 0.1 weight percent to about 1 weight percent. The added metal can be selected from the group of copper, silver, rhenium, tin, ruthenium and combinations thereof. Copper, silver, rhenium and tin are preferred because they do not substantially affect the activity of the nickel catalyst. The amount of reduced nickel in the catalytic dispersed phase may be at least about 20 weight percent, and more particularly at least about 50 weight percent. The porous support may be any porous support including, but not limited to, titania in the rutile form, zirconia in the monoclinic form, high-surface area granulated carbons, or boehmite.

The method for making the stabilized nickel catalyst involves forming a porous support with the deposited reduced nickel dispersed phase followed by depositing the additional metal upon the porous support. According to certain embodiments the deposition of the additional metal is separate and distinct from forming the porous support with an amount of reduced nickel metal catalyst dispersed phase. Specifically, the reduced nickel metal catalyst phase may be applied to a support or the reduced nickel metal catalyst phase and support may be co-precipitated. However, the additional metal deposition occurs separately from the formation of the supported reduced nickel metal catalyst phase and may be accomplished by impregnation of the porous support with soluble salts of the additional metal followed by reduction of the salt to the metal form. Salt solution is wetted onto the surface of the catalyst and goes into the pores of the catalyst and then the catalyst support is dried.

The hydrogenation step can be performed as a batch operation or as a continuous flow operation. In the case of a batch operation, the particular time required to achieve the desired substantially complete conversion varies depending upon the other reaction conditions but, for example, may range from about 30 to about 300 minutes. In the case of continuous flow operation with a catalyst bed reactor, the space velocity through the reactor varies depending upon the other reaction conditions but, for example, may range from about 0.5 to about 5 liter/liter/hour LHSV.

The hydrogenolysis step involves heating the hydrogenation product (typically alditol(s)) in the presence of hydrogen and a catalyst. The hydrogenolysis is continued until a desired amount of the alditol(s) are converted to low carbon polyol(s). For example, at least about 50, more particularly at least about 70, weight percent of the alditol(s) may be converted to polyol(s).

According to specific embodiments of the hydrogenolysis, the hydrogenation product is heated at a temperature of about 150 to about 300° C., more particularly about 180 to about 240° C. The system pressure during the hydrogenation step may also vary and could range, for example, between about 500 to about 3000 psig. The hydrogen reactant typically may be contacted with the hydrogenation product or alditol(s) by introducing a hydrogen gas flow into the reaction system via known means. The hydrogen may be fed into the reaction system with an overpressure in order to maintain the desired reaction system pressure.

The pH of the hydrogenolysis reaction medium may be neutral or basic. A base may be added during the hydrogenolysis reaction in order to control the pH. Exemplary bases include alkali metal-containing compounds or alkaline earth-containing compounds. Illustrative bases include CaOH, KOH and NaOH. The base can be added in an amount sufficient to control the reaction medium within the desired pH ranges. For example, up to about 1 weight percent base may be added during the hydrogenolysis reaction, based on the total weight of the reaction mixture.

The hydrogenolysis catalyst may be any catalyst capable of promoting hydrogenolysis of alditol(s). Illustrative hydrogenolysis catalysts include those described above in connection with the hydrogenation step. In any specific embodiment, the hydrogenation catalyst and hydrogenolysis catalyst may be the same or different. According to a certain embodiment, the ruthenium on rutile catalyst may be used for the hydrogenation step and the stabilized nickel metal catalyst may be used for the hydrogenolysis step.

The hydrogenolysis step can be performed as a batch operation or as a continuous flow operation. In the case of a batch operation, the particular time required to achieve the desired substantially complete conversion varies depending upon the other reaction conditions but, for example, may range from about 15 to about 300 minutes. In the case of continuous flow operation with a catalyst bed reactor, the space velocity through the reactor varies depending upon the other reaction conditions but, for example, may range from about 0.5 to about 4 liter/liter/hr LHSV.

As mentioned above, the product at the end of the hydrogenolysis typically may contain a mixture of lower carbon polyhydric alcohols such as ethylene glycol, propylene glycol, and glycerol, with a minimal amount of other byproducts. According to certain embodiments, the conversion end product mixture can contain at least about 60 weight percent ethylene glycol, propylene glycol and glycerol. The constituents of the conversion end product mixture can be isolated via any separation and/or purification technique such as, for example, distillation.

The steps of the disclosed conversion scheme may be performed in a continuous manner or in a batch manner. The process steps of the disclosed embodiments are typically carried out in an aqueous medium. The reactants in each step may be contacted with the respective catalysts via known techniques involving continuous catalytic reactors such as fixed beds, fluidized beds or expanded beds. Alternatively, the catalysts may be in any of several solid forms (such as a powder, granule, extrudate or tablet) or suspensions (such as a slurry) that are mixed with the reactants.

Having illustrated and described the principles of our invention with reference to several embodiments, it should be apparent to those of ordinary skill in the art that the invention may be modified in arrangement and detail without departing from such principles.

What is claimed is:

1. A continuous method for producing at least one polyol from lactose comprising:
   (a) catalytically hydrolyzing lactose to produce a hydrolyzate that includes at least one monosaccharide;

(b) subsequently hydrogenating the hydrolyzate to produce an alditol-containing intermediate composition; and (c) hydrogenolyzing the alditol-containing intermediate composition to produce at least one polyol, wherein steps (b) and (c) are performed in the presence of a catalyst having a support selected from titania in the rutile form, zircoma in the monoclinic form, high-surface area granulated carbon or boehmite.

2. A method according to claim 1 wherein step (a) comprises hydrolyzing lactose to convert about 90 to about 100 weight % of the lactose into monosaccharide.

3. A method according to claim 1 wherein step (a) is completed prior to initiation of step (b).

4. A method according to claim 1 wherein step (c) is performed in the presence of a catalyst comprising a plurality of porous particles on which are deposited (i) a nickel metal or reduced nickel as a dispersed phase and (ii) an additional metal as an additional dispersed phase.

5. A method according to claim 1 wherein the polyol comprises ethylene glycol, propylene glycol or glycerol.

6. A method according to claim 1 wherein the hydrolyzate comprises a mixture of glucose and galactose.

7. A method according to claim 1 wherein the alditol-containing intermediate composition comprises a mixture of sorbitol and dulcitol.

8. A method according to claim 1 further comprising providing the lactose in an aqueous composition that includes at least about 15 dry solids weight percent lactose based on the total weight of the aqueous composition.

9. A method according to claim 1 wherein step (c) further comprises adding a base to the alditol-containing intermediate composition.

10. A method according to claim 1 wherein steps (a), (b) and (c) are performed in an aqueous medium.

11. A method for producing at least one polyol from lactose comprising:
(a) hydrolyzing lactose to produce a hydrolyzate that includes at least one monosaccharide;
(b) catalytically hydrogenating the hydrolyzate to produce an alditol-containing intermediate composition, wherein the hydrogenation catalyst comprises ruthenium disposed on a titania support; and
(c) hydrogenolyzing the alditol-containing intermediate composition to produce at least one polyol.

12. A method according to claim 11 wherein the polyol comprises ethylene glycol, propylene glycol or glycerol.

13. A method according to claim 11 wherein the hydrolyzate comprises a mixture of glucose and galactose.

14. A method according to claim 11 wherein the alditol-containing intermediate composition comprises a mixture of sorbitol and dulcitol.

15. A method according to claim 11 further comprising providing the lactose in an aqueous composition that includes at least about 15 dry solids weight percent lactose based on the total weight of the aqueous composition.

16. A method according to claim 11 wherein the hydrogenation catalyst comprises ruthenium disposed on a rutile support.

17. A method according to claim 11 wherein step (c) is performed in the presence of a catalyst comprising a plurality of porous particles on which are deposited (i) a nickel metal or reduced nickel as a dispersed phase and (ii) an additional metal as an additional dispersed phase.

18. A method for producing at least one lower carbon polyhydric alcohol from lactose comprising:
(a) catalytically hydrolyzing lactose to produce a hydrolyzate that includes at least one monosaccharide, wherein the hydrolysis catalyst comprises a solid acid or an enzyme;
(b) subsequently catalytically hydrogenating the hydrolyzate to produce an alditol-containing intermediate composition, wherein the hydrogenation catalyst comprises ruthenium disposed on a titania support; and
(c) hydrogenolyzing the alditol-containing intermediate composition to produce at least one lower carbon polyhydric alcohol.

19. A method according to claim 18 wherein the hydrolyzate comprises a mixture of glucose and galactose.

20. A method according to claim 18 wherein the alditol-containing intermediate composition comprises a mixture of sorbitol and dulcitol.

21. A method according to claim 18 further comprising providing the lactose in an aqueous composition that includes at least about 15 dry solids weight percent lactose based on the total weight of the aqueous composition.

22. A method according to claim 18 wherein steps (a), (b) and (c) are performed in an aqueous medium.

23. A method for producing at least one polyol from lactose comprising:
(a) heating lactose in the presence of water and an enzyme to produce a first intermediate;
(b) subsequently heating the first intermediate in the presence of hydrogen and a catalyst to produce a second intermediate; and
(c) heating the second intermediate in the presence of hydrogen, a catalyst, and a base to produce at least one polyol,
wherein the catalyst in step (b) comprises ruthenium disposed on a titania support.

24. A method according to claim 23 wherein the enzyme in step (a) comprises immobolized β-galactosidase.

25. A method according to claim 23 wherein step (a) is performed in an aqueous medium with a pH of about 3 to about 7.

26. A method according to claim 23 wherein step (b) comprises heating the first intermediate at a temperature of about 80 to about 180° C.

27. A method according to claim 23 wherein step (c) comprises heating the second intermediate at a temperature of about 150 to about 300° C.

28. A method according to claim 27 wherein the catalyst in step (c) comprises a plurality of porous particles on which are deposited (i) a nickel metal or reduced nickel as a dispersed phase and (ii) an additional metal as an additional dispersed phase.

29. A method according to claim 18, wherein the enzyme comprises an immobilized enzyme.

30. A method according to claim 23, wherein the enzyme comprises an immobilized enzyme.

31. A method according to claim 18 wherein the solid acid catalyst is selected from an ion exchange resin and a perfluorinated polymeric resin.

32. A method according to claim 18 wherein the enzyme comprises immobilized β-galactosidase.

33. A method according to claim 18 wherein step (a) does not include adding a liquid acid.

34. A method according to claim 11 wherein step (c) further comprises adding a base to the alditol-containing intermediate composition.

35. A method according to claim 18 wherein step (c) further comprises adding a base to the alditol-containing intermediate composition.

* * * * *